US007301041B2

(12) United States Patent
Chaix-Bauvais et al.

(10) Patent No.: US 7,301,041 B2
(45) Date of Patent: Nov. 27, 2007

(54) BI-FUNCTIONAL METALLOCENES, PREPARATION PROCESS AND USE IN THE LABELING OR BIOLOGICAL MOLECULES

(75) Inventors: Carole Chaix-Bauvais, Chaponnay (FR); Corinne Moustrou, Marseilles (FR); Aude-Emmanuelle Navarro, Marseilles (FR); Hugues Brisset, Saint Cyr sur Mer (FR); Francis Garnier, Champigny sur Marne (FR); Bernard Mandrand, Villeurbanne (FR); Nicolas Spinelli, Lyons (FR)

(73) Assignee: Bio Merieux, Marcy l'Etoile (FR)

( * ) Notice: Subject to any disclaimer, the term of this patent is extended or adjusted under 35 U.S.C. 154(b) by 472 days.

(21) Appl. No.: 10/501,347

(22) PCT Filed: Feb. 14, 2003

(86) PCT No.: PCT/FR03/00484

§ 371 (c)(1),
(2), (4) Date: Oct. 13, 2004

(87) PCT Pub. No.: WO03/068787

PCT Pub. Date: Aug. 21, 2003

(65) Prior Publication Data

US 2005/0038234 A1    Feb. 17, 2005

(30) Foreign Application Priority Data

Feb. 14, 2002    (FR) .................................. 02 01858

(51) Int. Cl.
*C07F 17/02*    (2006.01)
*C07K 1/00*    (2006.01)
(52) U.S. Cl. ...................... 556/136; 556/144; 530/402; 536/25; 536/32
(58) Field of Classification Search ................ 556/136, 556/144; 536/25.32; 530/402
See application file for complete search history.

(56) References Cited

U.S. PATENT DOCUMENTS

| 6,211,356 B1 | 4/2001 | Wiessler et al. |
| 6,232,062 B1 | 5/2001 | Kayyem et al. |

FOREIGN PATENT DOCUMENTS

| FR | 2 607 507 | 6/1988 |
| WO | WO 00/31750 | 6/2000 |
| WO | WO 00/52063 | 9/2000 |
| WO | WO 01/81446 A1 | 11/2001 |

OTHER PUBLICATIONS

Keana et al., J. Am. Chem. Soc., vol. 108, No. 25, pp. 7951-7957 (1986).*

Fan, Rui-Ian et al.; "Synthesis and characterization of rare earth metal complexes of 1,1'-ferrocenediacetyl hydroxylamine"; XP-002216436.

Michel Egholm et al.; "Peptide Nuclelic Acids (PNA), Oligonucleotide Analogues with an Achiral Peptide Backbone"; J. Am. Chem. Soc. 1992, 114, 1895-1897.

Steven A. Kates et al.; "Solid-Phase Synthesis A Practical Guide"; Marcel Dekker, Inc.; 2000.

Serge L. Beaucage et al.; "Current Protocols in Nucleic Acid Chemistry (vol. 1)"; John Wiley & Sons, Inc., New York 1999.

Sudhir Agrawal; "Protocols for Oligonucleotides and Analogs Synthesis and Properties"; Methods in Molecular Biology, Humana Press, 1993.

Theodora W. Greene et al.; Protective Groups in Organic Synthesis Second Edition, Wiley Interscience.

Denis Guillaneux et al.; "High Yield Synthesis of Monosubstituted Ferrocenes"; J. Org. chem., 1995, 60, 2502-2505.

M.D. Matteucci et al.; "Synthesis of Deoxyoligonucleotides on a Polymer Support"; J. Am Chem. Soc. 1981, 103, 3185-3191.

(Continued)

*Primary Examiner*—Porfirio Nazario-Gonzalez
(74) *Attorney, Agent, or Firm*—Oliff & Berridge PLC

(57) ABSTRACT

The invention relates to bi-functionalised metallocenes of general formula (I) where Me=a transition metal, preferably chosen from Fe, Ru and Os, Y and Z, when identical are selected from $-(CH_2)_n-O-$, $(CH_2)-O-[(CH_2)_2-O]_p-$ and $-(CH_2)_q-CONH-(CH_2)_r-O-$, or $Y=-(CH_2)_s-NH-$ and $Z=-(CH_2)_t-COO-$, $n$=a whole number from 3 to 6 inclusive, p=a whole number from 1 to 4 inclusive, q=a whole number from 0 to 2 inclusive, r=a whole number from 0 to 2 inclusive, s=a whole number from 2 to 5 inclusive, t=a whole number from 3 to 6 inclusive, R and R'=H atoms or are protective groups used in oligonucleotide and peptide synthesis, where at least one of R or R' is protective group used in oligonucleotide and peptide synthesis and R and R' are as defined below: (i) when Z and Y are selected from $(CH_2)_n-O-$, $-(CH_2)-O-[(CH_2)_2-O]_p-$ and $-(CH_2)_q-CONH-(CH_2)_r-O-$, then R and R' are protective groups used in oligonucleotide synthesis and R is a group which can leave a free OH group after deprotection, preferably a photolabile group such as monomethroxythoxytrityl, dimethoxytrityl, t-butyldimethylsilyl, acetyl or trifluroacetyl, and R' is a phosphorylated group which can react with a free OH, preferably a phosphodiester, phosphoramidite or H-phosphonate and (ii) when $Y=-(CH_2)_s-NH-$ and $Z=-(CH_2)_t-COO-$, then R is a protective group used in the synthesis of peptides and is an amino-protecting group, preferably 9-fluorenyloxycarbonyl, t-butoxycarbonyl or benzyloxycarbonyl and R'=H. The above is applied in marking.

27 Claims, 1 Drawing Sheet

OTHER PUBLICATIONS

Figure 1:
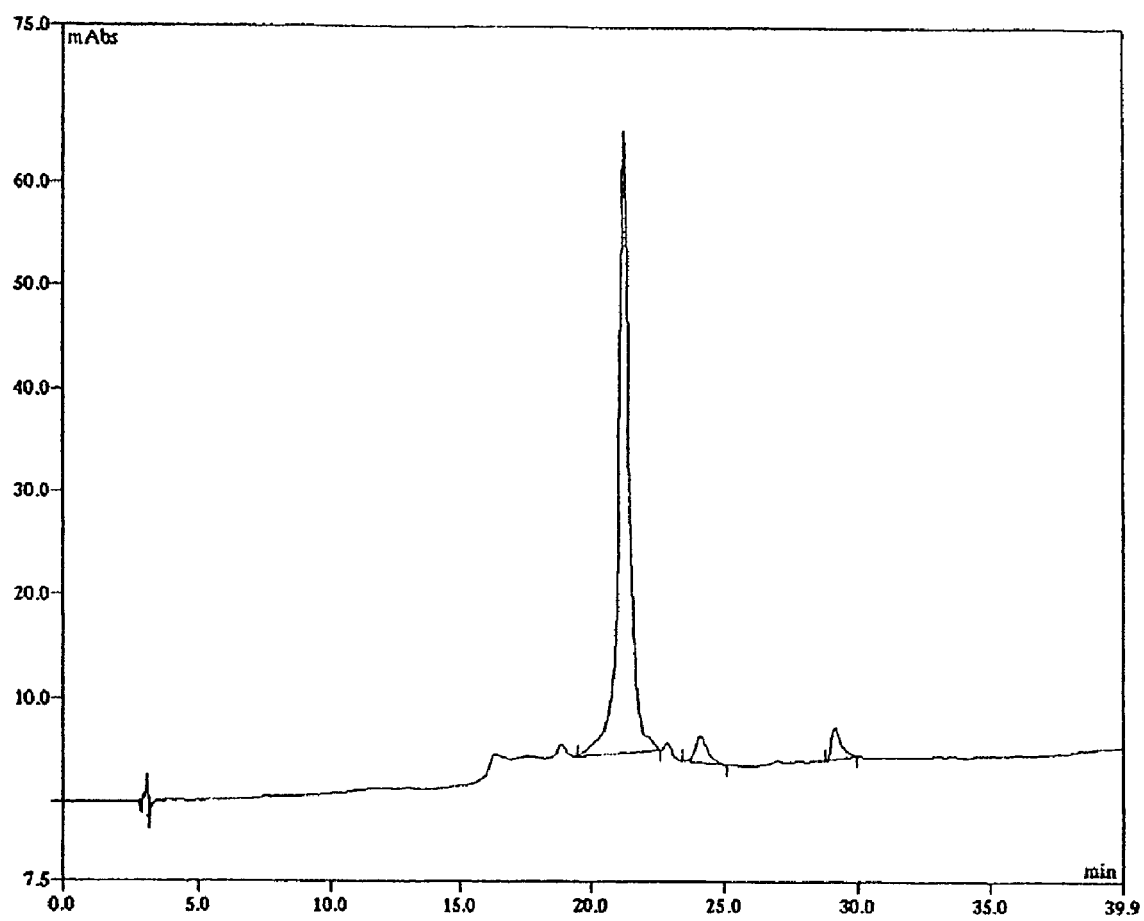

Ekkehard Lindner et al.; "Synthesis, Structure, and Electrochemistry of Osmametallocenophanes with Different Ring Size"; XP-002216435; Organometallics 1999, 18, 480-189.

Ekkehard Lindner et al.; "Preparation, properties, and reactions of metal-containing heterocycles Part C.V. Synthesis and structure of polyoxadiphosphaplatinaferrocenophanes"; Journal of Organometallic Chemistry 630 (2001) 206-274.

C.J. Yu et al.; "2'-Ribose-Ferrocene Oligonucleotides for Electronic Detection of Nucleic Acids"; J. Org. Chem. 2001, 66, 2937-2942.

* cited by examiner

SEQUENCE LISTING

```
<160> NUMBER OF SEQ ID NOS: 1

<210> SEQ ID NO 1
<211> LENGTH: 22
<212> TYPE: DNA
<213> ORGANISM: Unknown
<220> FEATURE:
<223> OTHER INFORMATION: ODN 7

<400> SEQUENCE: 1
tggaatactc aggttcctta tg                                          22
```

BI-FUNCTIONAL METALLOCENES, PREPARATION PROCESS AND USE IN THE LABELING OR BIOLOGICAL MOLECULES

The present invention relates to the field of labeling, in particular of biological molecules of interest, such as oligonucleotides and peptides. More particularly, a subject matter of the invention is novel bifunctionalized metallocenes, their process of preparation, their use in the labeling of oligonucleotides or of peptides and the labeled oligonucleotides and peptides thus obtained, and a support, functionalized by at least one metallocene of the invention, for supported synthesis.

Metallocenes are known as labels for oligonucleotides, in particular for the detection of DNA or RNA fragments.

Thus, for example, patent U.S. Pat. No. 6,211,356 discloses the use of a monofunctional metallocene exhibiting the phosphoramidite functional group for conferring, after coupling, a signal on DNA and/or RNA which will then be detectable using an electron microscope. The addition of the metallocene to the oligonucleotide is carried out manually and only at the chain end.

Patent application U.S. Pat. No. 6,232,062 discloses oligonucleotide-ferrocene conjugates as electrochemical probe for detecting hybridization. Said conjugates are obtained by supported synthesis starting from a uridine modified by a ferrocene and used as synthon. The two synthons described are a uridine 3'-phosphoramidite having a ferrocene in the 5-position and a uridine 3'-phosphoramidite having a ferrocene in the 2'-position. The production of oligonucleotides labeled by a ferrocene using this technique has the disadvantage of a high cost because of the use of a nucleoside modified by a ferrocene as synthon (monomer compatible with the synthesis), which is complex to prepare.

Chemically-modified phosphoramidites comprising a ferrocene substituent in the 2'-position of the ribose are known from C. J. Yu et al. (J. Org. Chem., 2001, 66, 2937-2942). These phosphoramidites make it possible to synthesize oligonucleotides comprising ferrocenes at various positions but the syntheses of these phosphoramidites involve synthetic techniques with protection and deprotection of the amine functional groups of the heterocycle and of the other free OH functional groups and require carrying out the syntheses under conditions which make it possible to retain the selectivity of the substitution.

Patent applications WO 00/31750 and WO 01/81446 disclose bifunctionalized ferrocenes as observable electrochemical probe, which ferrocenes are grafted to a polypyrrole, on the one hand, and to an oligonucleotide, on the other hand. The coupling of the ferrocene to the oligonucleotide is carried out between the activated ester (N-hydroxyphthalimide) of the ferrocene and the $NH_2$ ending of the presynthesized oligonucleotide. This coupling has the disadvantages that it is not compatible with the automated synthesis of oligonucleotides and that it lacks selectivity (side reactions on the amines of the bases).

The supported synthesis of metallocene/oligonucleotide or metallocene/peptide conjugates with the metallocenes used in the prior art is tedious as it requires the synthesis of a nucleoside modified by a ferrocene and then of the corresponding phosphoramidite synthon. Furthermore, the coupling of metallocene to oligonucleotides or peptides is not always selective, so that it cannot be automated on current commercial synthesizers.

The Applicant Company has now discovered novel bifunctionalized metallocenes which make it possible to overcome the disadvantages due to the metallocenes of the prior art, namely that they make possible:

automated synthesis of metallocene/oligonucleotide or metallocene/peptide conjugates, selective coupling between the metallocene and the oligonucleotide or the metallocene and the peptide, and an improvement in the production costs of said conjugates as the synthon used is the metallocene as is and not in the form of a nucleoside modified by a metallocene.

Thus, a subject matter of the present invention is metallocenes of formula (I):

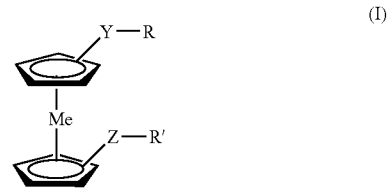

in which

Me represents a transition metal, preferably chosen from Fe, Ru and Os,

Y and Z, which are identical, are chosen from $-(CH_2)_n-O-$, $-(CH_2)-O-[(CH_2)_2-O]_p-$ and $-(CH_2)_q-CONH-(CH_2)_r-O-$, or else Y is $-(CH_2)_s-NH-$ and Z is $-(CH_2)_t-COO-$, n is an integer between 3 and 6, p is an integer between 1 and 4, q is an integer between 0 and 2, r is an integer between 0 and 2, s is an integer between 2 and 5, t is an integer between 3 and 6, R and R' represent hydrogen atoms or are protective groups used in the synthesis of oligonucleotides and peptides and are as defined below:

(i) when Z and Y are chosen from $-(CH_2)_n-O-$, $-(CH_2)-O-[(CH_2)_2-O]_p-$ and $-(CH_2)_q-CONH-(CH_2)_r-O-$, R is a group capable of leaving a free hydroxyl group after deprotection, preferably a photolabile group, monomethoxytrityl, dimethoxytrityl, tert-butyldimethylsilyl, acetyl or trifluoroacetyl, and R' is a phosphorus group capable of reacting with a free hydroxyl group, preferably a phosphodiester, phosphoramidite or H-phosphonate group, and (ii) when Y is $-(CH_2)_s-NH-$ and Z is $-(CH_2)_t-COO-$, R represents a protective group for amines, preferably 9-fluorenyloxycarbonyl, tert-butoxycarbonyl or benzyloxycarbonyl, and R' represents a hydrogen atom.

Another subject matter of the invention is a process for the preparation of a metallocene of the invention, characterized in that it comprises the following stages:

(i) when Z and Y are chosen from $-(CH_2)_n-O-$, $-(CH_2)-O-[(CH_2)_2-O]_p-$ and $-(CH_2)_q-CONH-(CH_2)_r-O-$:

a stage of protection of one of the hydroxyl groups of a compound of general formula (II):

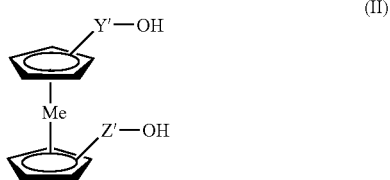

(II)

in which Me is as defined above,

Y' and Z', which are identical, are chosen from —$(CH_2)_n$—, —$(CH_2)$—O—$[(CH_2)_2$—O$]_{p'}$—$(CH_2)_2$— and —$(CH_2)_q$—CONH—$(CH_2)_r$—, n, q and r are as defined above and p' is an integer between 0 and 3, by attachment of a group capable of leaving a free hydroxyl group after deprotection, preferably chosen from a photolabile group, monomethoxytrityl, dimethoxytrityl, tert-butyldimethylsilyl, acetyl and trifluoroacetyl, and a stage of coupling to the other hydroxyl group left free, a phosphorus group capable of reacting with a free hydroxyl group, preferably chosen from the phosphodiester, phosphoramidite and H-phosphonate groups; and (ii) when Y is —$(CH_2)_s$—NH— and Z is —$(CH_2)_t$—COO—:

a stage of protection of the $NH_2$ group of a compound of general formula (III):

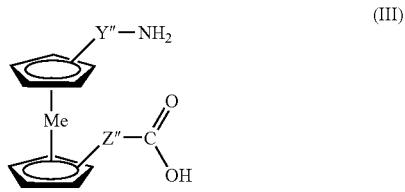

(III)

in which
Me is as defined above,
Y" is —$(CH_2)_s$— and
Z" is —$(CH_2)_t$—,
s and t being as defined above, by attachment of a group capable of leaving a free amine functional group after deprotection, preferably chosen from 9-fluorenyloxycarbonyl, tert-butoxycarbonyl and benzyloxycarbonyl.

Another subject matter of the invention is a (bis)-hydroxymetallocene of general formula (II) as described above.

Another subject matter of the invention is a process for labeling:

an oligonucleotide with the bifunctionalized metallocene of formula (I), in which Y and Z, which are identical, are chosen from —$(CH_2)_n$—O—, —$(CH_2)$—O—$[(CH_2)_2$—O$]_{p'}$— and —$(CH_2)_q$—CONH—$(CH_2)_r$—O—, comprising the substitution of one or more nucleotide synthons by one or more of said metallocenes of formula (I) in the cycle for the synthesis of said oligonucleotide, and a peptide with a bifunctionalized metallocene of formula (I), in which Y is —$(CH_2)_s$—NH— and Z is —$(CH_2)_t$—COO—, comprising the substitution of one or more amino acid synthons by one or more of said metallocenes of formula (I) in the cycle for the synthesis of said peptide, and the oligonucleotides and peptides thus labeled.

Another subject matter of the invention is a support for the synthesis of oligonucleotides or of peptides, functionalized at the surface by at least one metallocene of formula (I), respectively.

Before describing the invention in detail, certain terms used in the description and the claims are defined below.

The term "oligonucleotide" denotes a sequence of at least 2 natural or modified nucleotides (deoxyribonucleotides or ribonucleotides, or both) capable of hybridizing, under appropriate hybridization conditions, with an at least partially complementary oligonucleotide. The term "nucleoside" is understood to mean an organic compound consisting of a purine or pyrimidine base bonded to a monosaccharide (ribose or deoxyribose). The term "nucleotide" is understood to mean an organic compound consisting of a purine or pyrimidine base bonded to a monosaccharide (ribose or deoxyribose) and to a phosphate group. The term "modified nucleotide" is understood to mean, for example, a nucleotide comprising a modified base and/or comprising a modification at the internucleotide bond and/or on the backbone. Mention may be made, as example of modified base, of inosine, 5-methyldeoxycytidine, 5-(dimethylamino)deoxyuridine, 2,6-diaminopurine and 5-bromodeoxyuridine. Mention may be made, to illustrate a modified internucleotide bond, of phosphorothioate, N-alkylphosphoramidate, alkylphosphonate and alkyl-phosphotriester bonds. Alpha-oligonucleotides, such as those disclosed in FR-A-2 607 507, and the PNAs which form the subject of the paper by M. Egholm et al., J. Am. Chem. Soc. (1992), 114, 1895-1897, are examples of oligonucleotides composed of nucleotides possessing a modified backbone.

The term "peptide" means in particular any sequence of at least two amino acids, such as protein, protein fragment or oligopeptide, which has been extracted, separated, isolated or synthesized, such as a peptide obtained by chemical synthesis or by expression in a recombinant organism. Also included is any peptide in the sequence of which one or more amino acids of the L series are replaced by one or more amino acids of the D series, and vice versa; any peptide in which at least one of the CO—NH bonds is replaced by an NH—CO bond; any peptide in which at least one of the CO—NH bonds is replaced by an NH—CO bond, the chirality of each aminoacyl residue, whether or not involved in one or more of said CO—NH bonds, either being retained or inverted with respect to the aminoacyl residues constituting a reference peptide (or immunoretroids) and any mimotope.

Mention may be made, to illustrate the various classes of peptides concerned, of adrenocorticotropic hormones or their fragments, angiotensin analogs and their inhibitors, natriuretic peptides, bradykinin and its peptide derivatives, chemotactic peptides, dynorphin and its derivatives, endorphins and their derivatives, enkephalins and their derivatives, enzyme inhibitors, fibronectin fragments and their derivatives, gastrointestinal peptides, opioid peptides, oxytocin, vasopressin, vasotocin and their derivatives, or protein kinases.

The metallocenes of the invention are of use as synthon for the preparation of hapten derivatives or any other molecule which can be synthesized.

In particular, the metallocenes of the invention are of use in the supported synthesis of oligonucleotides and peptides. They make possible the labeling of oligonucleotides or peptide synthesized in a very selective way as a result of the two specific functional groups which they possess, namely two hydroxyl functional groups as shown in the formula (II) for the supported synthesis of oligonucleotides or else an amine functional group and an acid functional group as shown in the formula (III) for the supported synthesis of peptides.

In the case of the supported synthesis of oligonucleotides, the functionalized spacer arms Y and Z as shown in the formula (I) each have an oxy functional group giving a hydroxyl functional group after deprotection and Y and Z are chosen from —(CH$_2$)$_n$—O—, —(CH$_2$)—O—[(CH$_2$)$_2$—O]$_p$— and —(CH$_2$)$_q$—CONH—(CH$_2$)$_r$—O—.

In one embodiment of the invention, Y and Z are each —(CH$_2$)$_n$—O—, n being equal to 3.

According to another embodiment, Y and Z are each —(CH$_2$)—O—[(CH$_2$)$_2$—O]$_p$—, p being equal to 2.

In the case of the supported synthesis of peptides, the functionalized spacer arms Y and Z as indicated in the formula (I) have either an amide functional group giving an amine functional group after deprotection or an acid functional group and are chosen from —(CH$_2$)$_s$—NH— and —(CH$_2$)$_t$—COO—, it being understood that Y and Z cannot be identical.

According to one embodiment of the invention, s is equal to 3 and t is equal to 4.

The transition metal Me used in the metallocenes of formula (I) of the invention can be any transition metal. Preferably, it is chosen from Fe, Ru and Os.

According to one embodiment of the invention, Me is iron.

The protective groups used in the synthesis of the oligonucleotides and peptides are any group conventionally known to a person skilled in the art. They are described, for example, in Solid Phase Synthesis, A Practical Guide, Steven A. Kates and Fernando Albericio, published by Maral Dekker, 2000.

In the case of a metallocene of the invention of use as synthon in the synthesis of oligonucleotides, one of the protective groups must be a phosphorus group capable of reacting either with a free hydroxyl in the 5'- or 3'-position of the preceding nucleotide, insofar as the metallocene of the invention is placed after a nucleotide, or with a deprotected hydroxyl of the preceding metallocene, insofar as the oligonucleotide comprises several metallocenes in succession, or with a free hydroxyl of another chemical compound which can act, for example, as spacer arm, such as poly(ethylene oxide). Examples of such phosphorus protective groups comprise the phosphodiester, phosphoramidite and H-phosphonate groups, and their derivatives.

The other protective group of the metallocene must be capable of leaving a free hydroxyl group after deprotection in order to react either with a reactive phosphorus (phosphodiester, phosphoramidite, H-phosphonate) of the following nucleotide, insofar as the metallocene is placed before a nucleotide, or with a reactive phosphorus of the following metallocene, insofar as at least two metallocenes follow one another. Mention may be made, as example of this type of protective group, of photolabile groups, monomethoxytrityl, dimethoxytrityl, tert-butyldimethylsilyl, acetyl and trifluoroacetyl.

Mention may be made, as examples of photolabile group, of 6-nitroveratryl, 6-nitropiperonyl, methyl-6-nitroveratryl, nitroveratrylcarbonyl, methyl-6-nitropiperonyl, nitrobenzyl, nitrobenzyloxycarbonyl, dimethyldimethoxybenzyl, dimethyldimethoxybenzyloxycarbonyl, 5-bromo-7-nitroindolinyl, hydroxy-α-methylcinnamoyl, 2-(oxymethylene)anthraquinonyl or pyrenylmethoxycarbonyl.

Examples of protective group for amines comprise 9-fluorenyloxycarbonyl, tert-butoxycarbonyl and benzyloxycarbonyl.

A bifunctionalized metallocene of general formula (I):

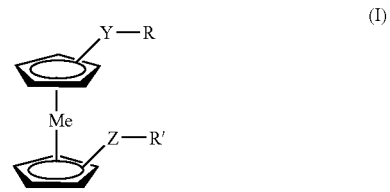

in which

Me represents a transition metal, preferably chosen from Fe, Ru and Os,

Y and Z, which are identical, are chosen from —(CH$_2$)$_n$—O—, —(CH$_2$)—O—[(CH$_2$)$_2$—O]$_p$— and —(CH$_2$)$_q$—CONH—(CH$_2$)$_r$—O—, or else Y is —(CH$_2$)$_s$—NH— and Z is —(CH$_2$)$_t$—COO—, n is an integer between 3 and 6, p is an integer between 1 and 4, q is an integer between 0 and 2, r is an integer between 0 and 2, s is an integer between 2 and 5, t is an integer between 3 and 6, R and R' represent hydrogen atoms or are protective groups used in the synthesis of oligonucleotides and peptides, it being understood that at least one of R or R' is a protective group used in the synthesis of oligonucleotides and peptides and that R and R' are as defined below:

(i) when Z and Y are chosen from —(CH$_2$)$_n$—O—, —(CH$_2$)—O—[(CH$_2$)$_2$—O]$_p$— and —(CH$_2$)$_q$—CONH—(CH$_2$)$_r$—O—, then R and R' are protective groups used in the synthesis of oligonucleotides, and R is a group capable of leaving a free hydroxyl group after deprotection, preferably a photolabile group, monomethoxytrityl, dimethoxytrityl, tert-butyldimethylsilyl, acetyl or trifluoroacetyl, and R' is a phosphorus group capable of reacting with a free hydroxyl group, preferably a phosphodiester, phosphoramidite or H-phosphonate group, and (ii) when Y is —(CH$_2$)$_s$—NH— and Z is —(CH$_2$)$_t$—COO—, then R is a protective group used in the synthesis of peptides and represents a protective group for amines, preferably 9-fluorenyloxycarbonyl, tert-butoxycarbonyl or benzyloxycarbonyl, and R' represents a hydrogen atom, constitutes a preferred subject matter of the invention.

The metallocenes of the invention are prepared by a process requiring one or two stages making it possible to obtain the desired protective groups on the appropriate functionalized spacer arms.

Thus, another subject matter of the present invention is a process for the preparation of a metallocene of the invention, characterized in that it comprises the following stages:

(i) when Z and Y are chosen from —(CH$_2$)$_n$—O—, —(CH$_2$)—O—[(CH$_2$)$_2$—O]$_p$— and —(CH$_2$)$_q$—CONH—(CH$_2$)$_r$—O—:

a stage of protection of one of the hydroxyl groups of a compound of general formula (II):

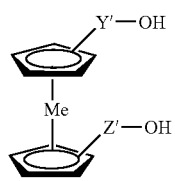

in which Me is as defined above,

Y' and Z', which are identical, are chosen from —(CH$_2$)$_n$—, —(CH$_2$)—O—[(CH$_2$)$_2$—O]$_{p'}$—(CH$_2$)$_2$— and —(CH$_2$)$_q$—CONH—(CH$_2$)$_r$—, n, q and r are as defined above and p' is an integer between 0 and 3, by attachment of a group capable of leaving a free hydroxyl group after deprotection, preferably chosen from a photolabile group, monomethoxytrityl, dimethoxytrityl, tert-butyldimethylsilyl, acetyl and trifluoroacetyl, and a stage of coupling, to the other hydroxyl group left free, a phosphorus group capable of reacting with a free hydroxyl group, preferably chosen from the phosphodiester, phosphoramidite and H-phosphonate groups; and (ii) when Y is —(CH$_2$)$_s$—NH— and Z is —(CH$_2$)$_t$—COO—:

a stage of protection of the NH$_2$ group of a compound of general formula (III):

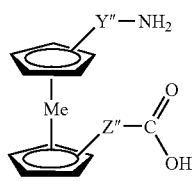

in which
Me is as defined above,
Y'' is —(CH$_2$)$_s$— and
Z'' is —(CH$_2$)$_t$—,
s and t being as defined above, by attachment of a group capable of leaving a free amine functional group after deprotection, preferably chosen from 9-fluorenyloxycarbonyl, tert-butoxycarbonyl and benzyloxycarbonyl.

The stage of protection of one of the hydroxyl groups of a compound of general formula (II) by a protective group capable of leaving a free hydroxyl group after deprotection, such as a photolabile group, monomethoxytrityl, dimethoxytrityl, tert-butyldimethylsilyl, acetyl and trifluoroacetyl, is carried out under conditions well known to a person skilled in the art, such as described in Current Protocols in Nucleic Acid Chemistry (Volume 1), John Wiley & Sons Inc., NY, 1999.

Likewise, the stage of coupling, to the other hydroxyl group left free of the compound of formula (II), a phosphorus protective group, such as a phosphodiester, phosphoramidite or H-phosphonate group, is carried out under conditions well known to a person skilled in the art, such as described in Current Protocols in Nucleic Acid Chemistry (Volume 1), John Wiley & Sons Inc., NY, 1999, and in Protocols for oligonucleotides and Analogs, Synthesis and Properties, edited by Sudhir Agrawal, Methods in Molecular Biology, Humana Press, 1993.

The specific compounds of formula (II) defined below are novel compounds which constitute another subject matter of the invention. They are chosen from the bis-(hydroxy) metallocenes of general formula (II):

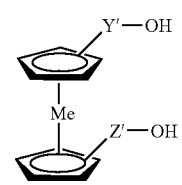

in which

Me is a transition metal, preferably chosen from Fe, Ru and Os,

Y' and Z', which are identical, are chosen from —(CH$_2$)$_n$—, (CH$_2$)—O—[(CH$_2$)$_2$—O]$_{p'}$—(CH$_2$)$_2$— and —(CH$_2$)$_q$—CONH—(CH$_2$)$_r$—, n is an integer between 3 and 6,
p' is an integer between 0 and 3,
q is an integer between 0 and 2, and
r is an integer between 0 and 2, it being understood that, when Me is Fe or Ru and when Y' and Z' are —(CH$_2$)$_n$—, then n is 5 and, when Me is Fe and when Y' and Z' are —(CH$_2$)—O—[(CH$_2$)$_2$—O]$_{p'}$—(CH$_2$)—, then p' is 0.

According to a preferred embodiment, the compounds of formula (II) have at least one of the following characteristics:

Me is iron, and

Y' and Z' are each —(CH$_2$)$_n$—, n being equal to 3, or else Y' and Z' are each —(CH$_2$)—O—[(CH$_2$)$_2$—O]$_{p'}$—(CH$_2$)$_2$—, p' being equal to 0.

The compounds of formula (II) can be obtained in different ways depending on the nature of the spacer arm Y' and Z'.

To obtain a metallocene with —(CH$_2$)$_n$— as spacer arms, aldehyde functional groups are grafted to a metallocene, then the compound thus obtained is reacted with an appropriate ethyl diethylphosphonoalkylate, to obtain a 1,1'-bis[(2-ethyloxycarbonyl)alkenyl]metallocene, and then two reduction stages are carried out, to reduce, first, the double bond and then to release the primary alcohol, as indicated below:

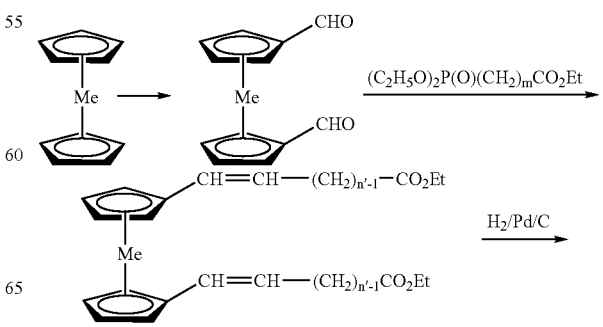

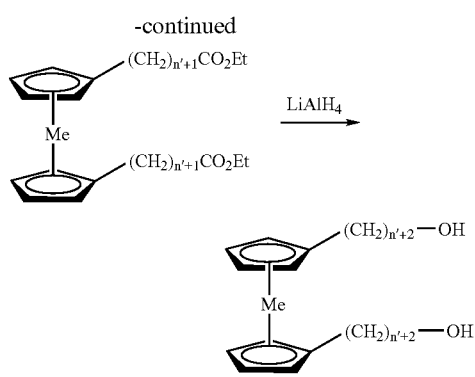

where Et is ethyl and n' is between 2 and 4.

To obtain a metallocene with —(CH$_2$)—O—[(CH$_2$)$_2$—O]$_{p-1}$-(CH$_2$)$_2$— as spacer arms, the hydroxyl groups of a bis-(hydroxymethyl)metallocene are functionalized to appropriate 2-chloroethyl(poly(ethylene oxide)) groups in the presence of a base, such as NaOH, then the chloro radical is converted to the iodo radical and then to the hydroxyl radical, as indicated below:

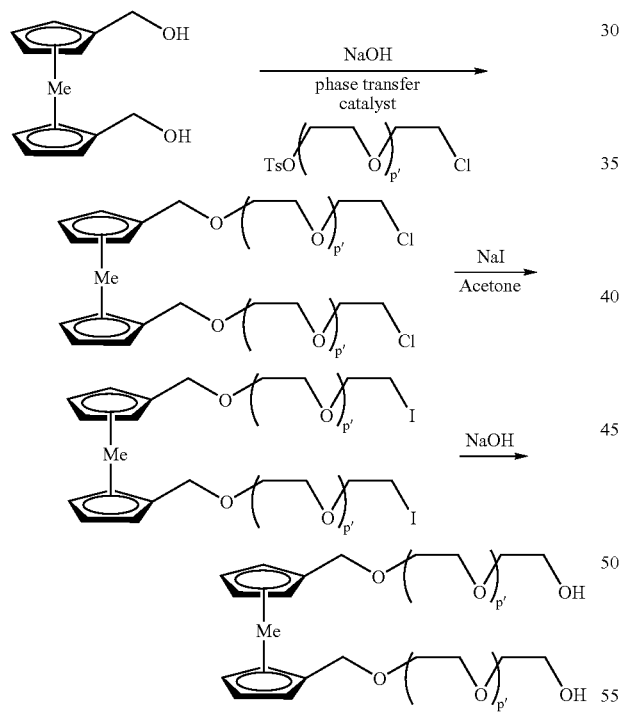

where Ts is tosyl and p' is an integer between 0 and 3.

To obtain a metallocene with —(CH$_2$)$_q$—CONH—(CH$_2$)$_r$—O— as spacer arms, an appropriate 1,1'-(N-hydroxyphthalimide-carbonylalkyl)metallocene, as obtained according to the procedure disclosed in application WO 01/81446, is treated with the appropriate trifluoroacetoxyalkylamine and then the trifluoroacetoxy radical is converted to the hydroxyl radical, as indicated below:

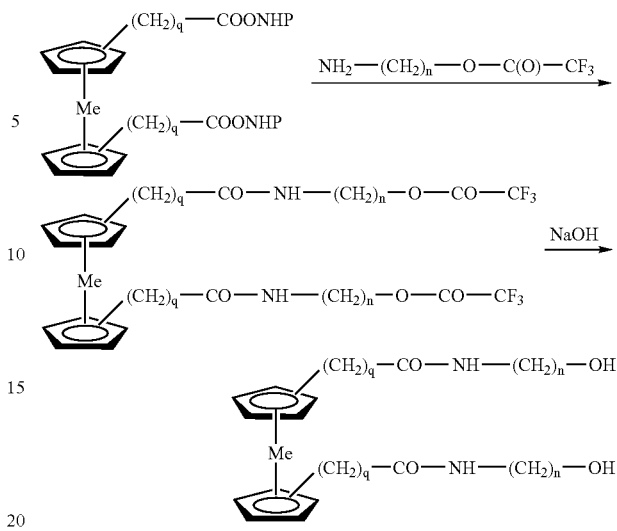

where q and r are as defined above.

The compound (III) can be produced according to the following procedure:

An appropriate 1-tert-butoxycarbonylaminoalkyl-1'-iodometallocene 1 is reacted with an organometallic iodide 2 and then, at the end of treatment, the acid functional group is released to give the compound (III), as indicated below:

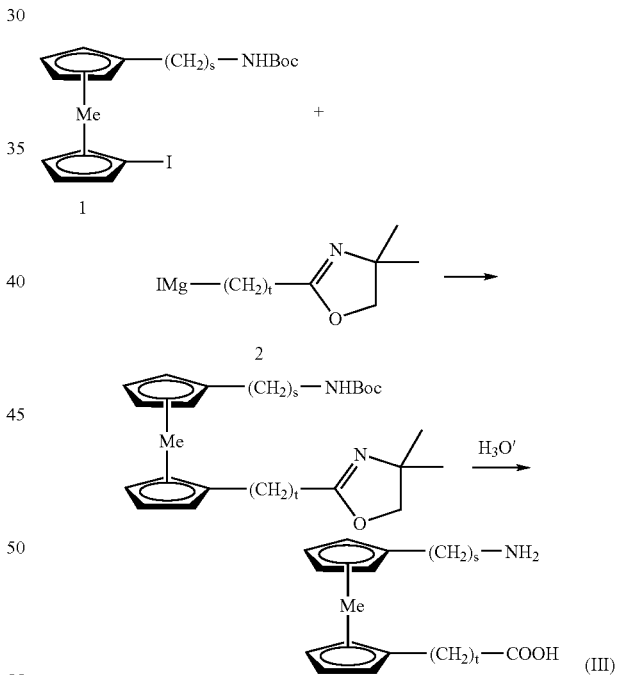

where s and t are as described above.

The compound 2 can itself be obtained according to the following synthesis:

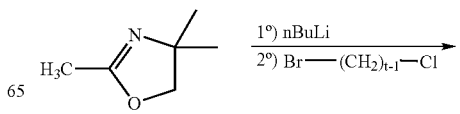

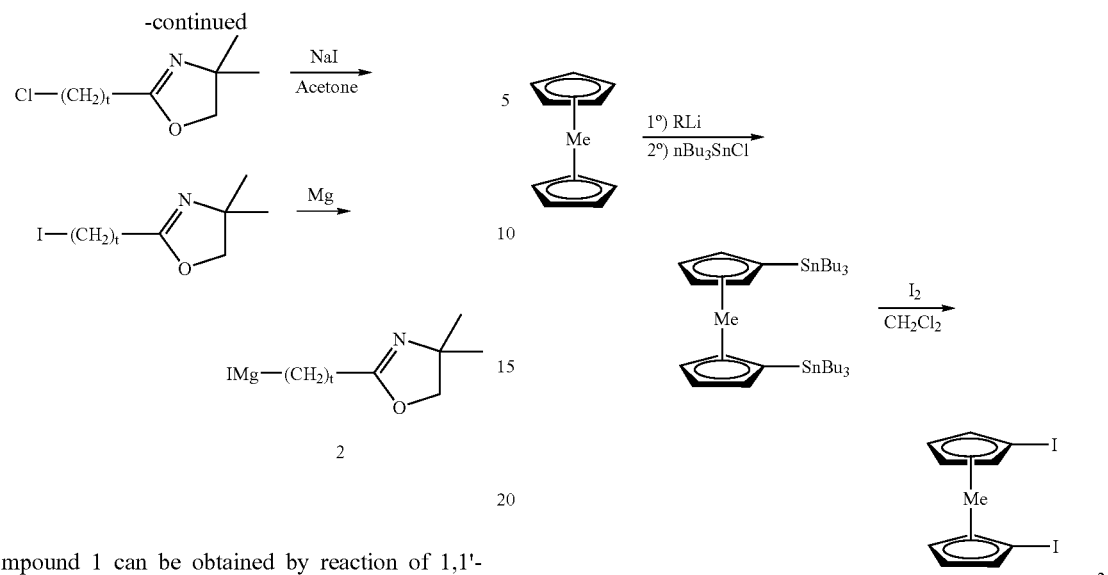

The compound 1 can be obtained by reaction of 1,1'-iodometallocene 3 with an organometallic iodide 4 as follows:

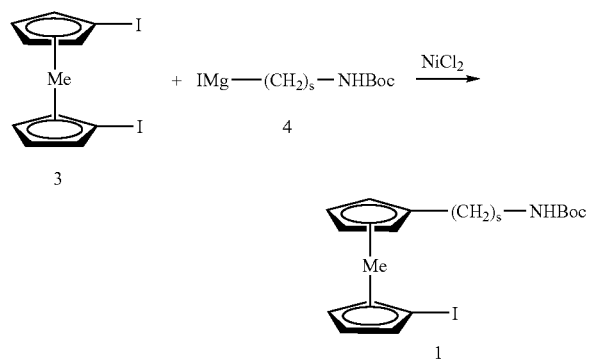

as described in:
a) "Comprehensive Organic Synthesis", volume 3, Barry M. Trost and Ian Fleming,
b) "Palladium Reagents and Catalysts", Juio Tsuji, Wiley & Sons, 1995.

The organometallic iodide 4 can itself be obtained from an alkylamine iodide in 2 stages, as follows:

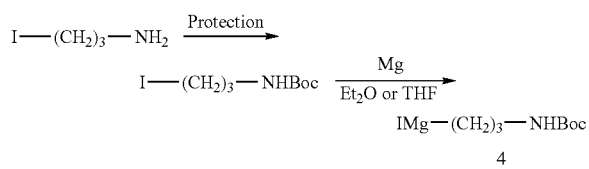

where s is as described above, as described in "Protective Groups in Organic Chemistry", Greene & Wuts, Third edition, Wiley Interscience.

Finally, 1,1'-iodometallocene 3 can itself be obtained according to the following procedure, as described in the paper by D. Guillaneux and H. B. Kagan, J. Org. Chem., 1995, 60, 2502-2505.

The metallocenes of formula (I) thus obtained can then be used for labeling, in particular biological molecules of interest, such as oligonucleotides and peptides, during their supported synthesis.

Thus, another subject matter of the invention is a process for labeling an oligonucleotide or peptide with a bifunctionalized metallocene of formula (I) of the invention, which process comprises the substitution of one or more nucleotide or amino acid synthons by one or more of said metallocenes of formula (I) in the cycle for the synthesis of said oligonucleotide or said peptide.

In the case of the synthesis of oligonucleotides, use is made of one or more metallocenes of formula (I) in which Y and Z, which are identical, are chosen from —$(CH_2)_n$—O—, —$(CH_2)$—O—$[(CH_2)_2$—O$]_p$— and —$(CH_2)_q$—CONH—$(CH_2)_r$—O—.

In the case of the synthesis of peptides, use is made of one or more metallocenes of formula (I) in which Y is —$(CH_2)_s$—NH— and Z is —$(CH_2)_t$—COO—.

The substitution of nucleotide or amino acid synthons by metallocenes of the invention can be carried out on current synthesizers at any position on the production line. According to one embodiment of the invention, the substitution fulfils at least one of the following conditions:

it is carried out in the 3'- or 5'-positions in the case of oligonucleotides or at the C-terminal or N-terminal ends in the case of peptides, and there are at least two consecutive substitutions.

The substitution can easily be carried out by a person skilled in the art as it consists solely in replacing a nucleotide or amino acid by a metallocene of the invention.

Thus, for example, in the case of the phosphoramidite coupling cycle as represented in scheme 1 below, any one of the nucleotides of this production line, or several, can be replaced by one or more metallocenes of formula (I) in which one of the protective groups R or R' is a phosphoramidite.

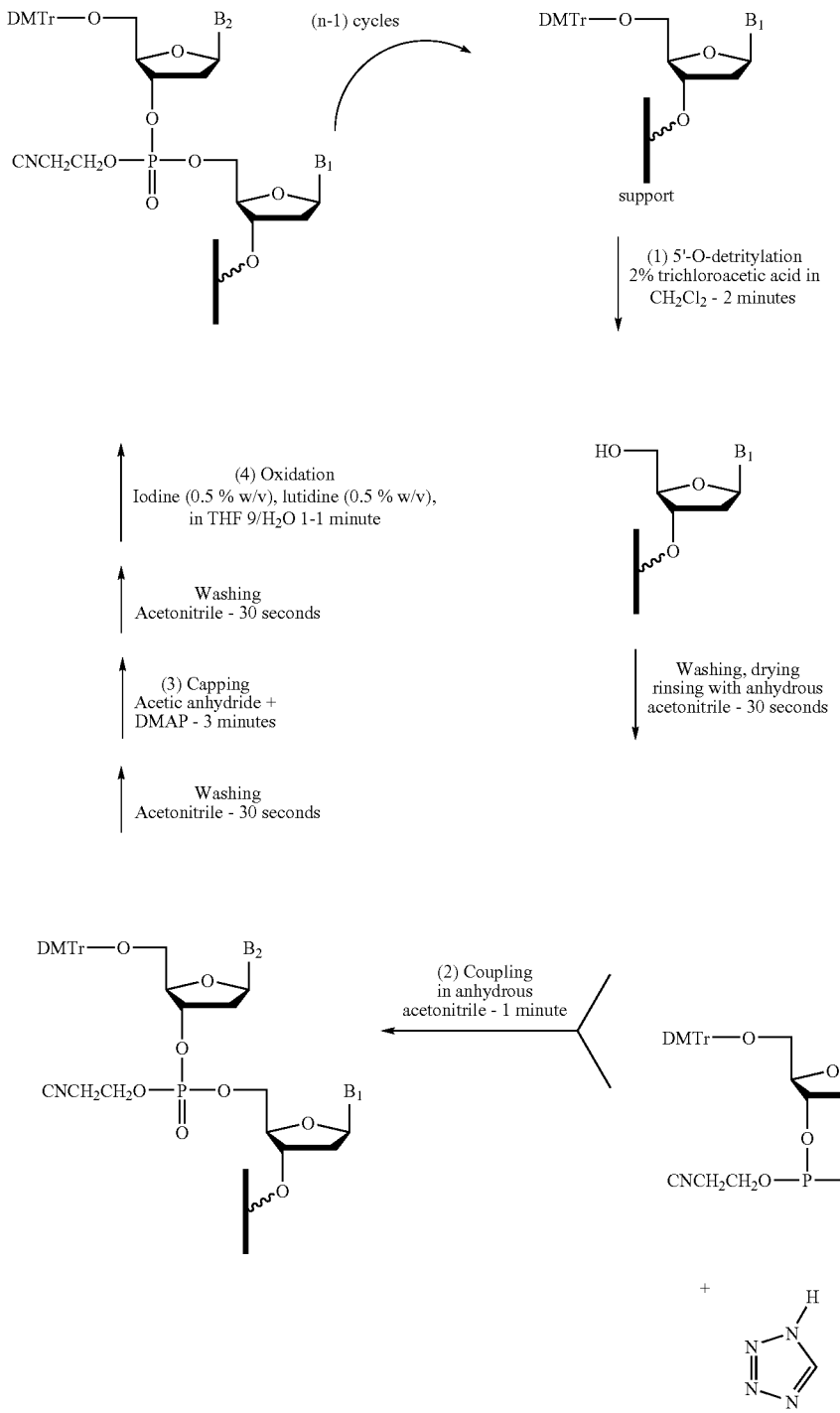
Scheme 1
Phosphoramidite coupling cycle
According to another example, in the case of the "H-phosphonate" series cycle as represented in scheme 2 below, any one of the nucleotides of this cycle, or several, can be replaced by one or more metallocenes of formula (I) in which one of the protective groups R or R' is an H-phosphonate.

Scheme 2
"H-Phosphonate" series cycle

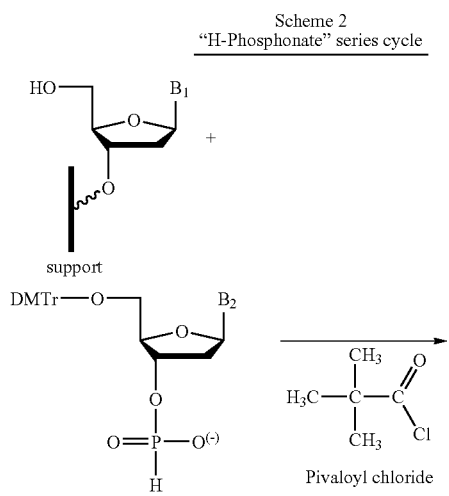

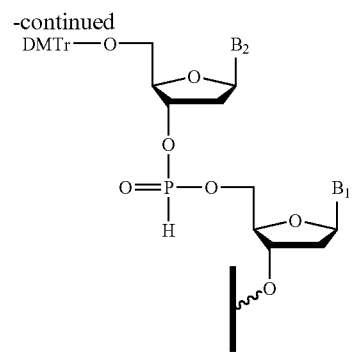

Likewise, according to another example, in the case of the "phosphotriester" coupling cycle as represented in scheme 3 below, any one of the nucleotides of this cycle, or several, can be replaced by one or more metallocenes of formula (I) in which one of the protective groups R or R' is a phosphodiester.

Scheme 3
Phosphotriester coupling cycle

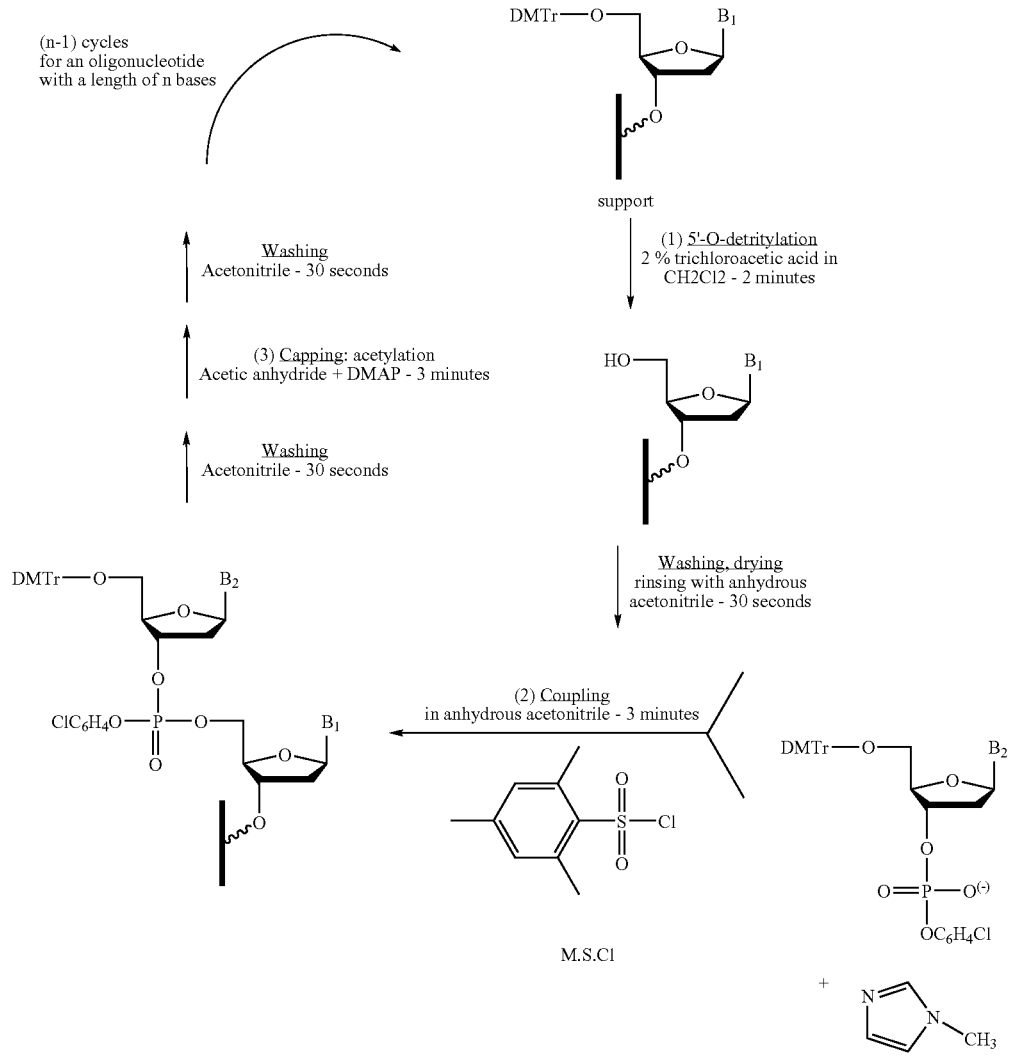

Likewise, a person skilled in the art can easily replace one or more amino acids by one or more metallocenes of the invention during known syntheses of peptides, such as the synthesis according to BOC (tert-butoxycarbonyl) or FMOC (9-fluorenyloxycarbonyl) chemistry.

The oligonucleotides and peptides as labeled by the metallocenes of the invention are novel and constitute another subject matter of the invention.

As above, the oligonucleotides are labeled with one or more metallocenes resulting from metallocenes of formula (I) in which Y and Z, each independently, are chosen from $-(CH_2)_n-O-$, $-(CH_2)-O-[(CH_2)_2-O]_p-$ and $-(CH_2)_q-CONH-(CH_2)_r-O-$, and the peptides are labeled with one or more metallocenes resulting from the metallocenes of formula (I) in which Y is $-(CH_2)_s-NH-$ and Z is $-(CH_2)_t-COO-$. The metallocenes of formula (II) of the invention are incorporated in the oligonucleotide sequences so as to replace, from a chemical viewpoint, the nucleosides in said sequences. Similarly, the metallocenes of formula (III) are incorporated in the peptide sequences so as to replace, from a chemical viewpoint, the amino acids in said sequences.

According to a preferred embodiment, the oligonucleotides or peptides of the invention comprise at least one metallocene of the invention in the 3'- or 5'-position or alternatively at the C-terminal or N-terminal ends, respectively.

In the case where the aim is to obtain an oligonucleotide labeled in the 3'-position, use may be made of a solid support to which is grafted at least one metallocene of the invention by covalent reaction of one of its functionalized ends. This support-metallocene complex constitutes another subject matter of the invention.

Use may be made, as support, of the support below LCAA-CPG (Long Chain Alkylamine Controlled Pore Glass), which is conventionally used in oligonucleotide synthesis.

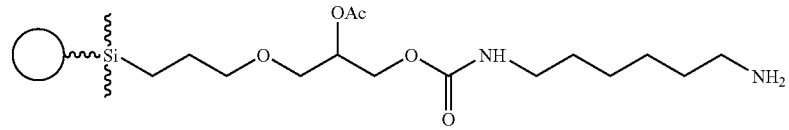

The grafting of the metallocene or metallocenes of the invention to the support can be carried out, for example, according to the following procedure:

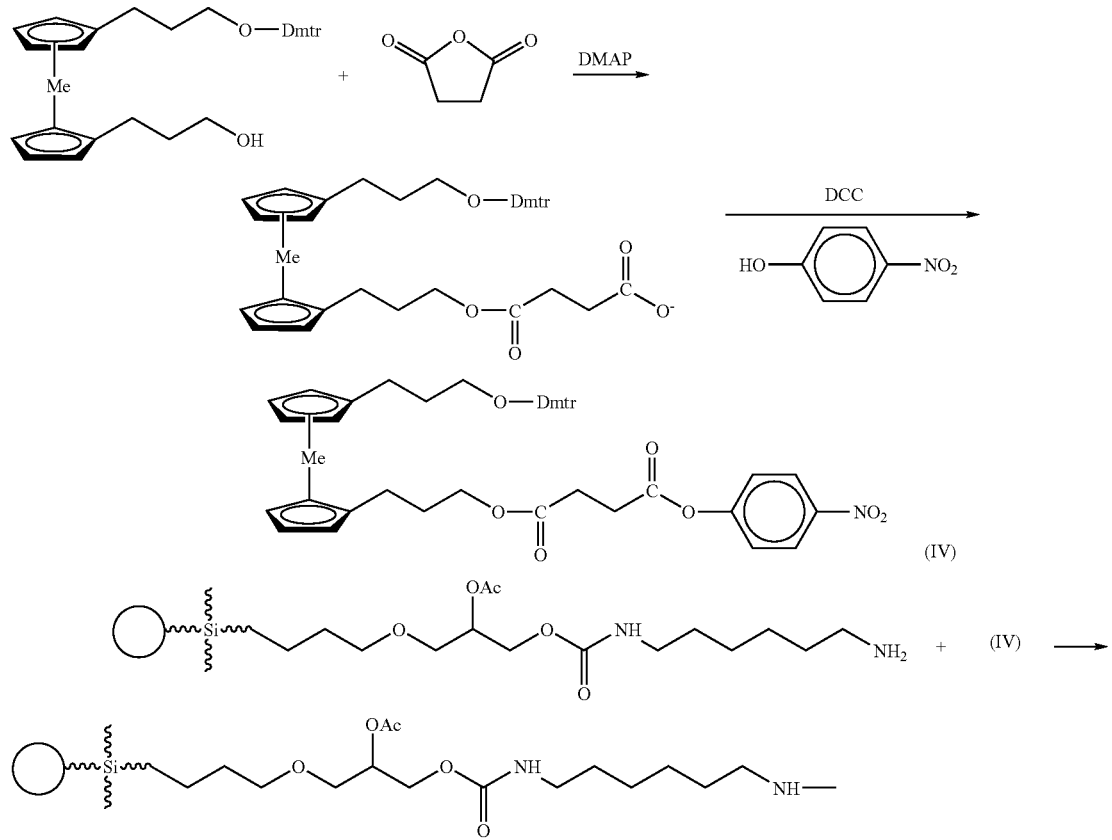

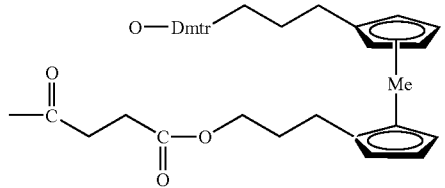

where Dmtr is dimethoxytrityl, DMAP is dimethylaminopyridine and DCC is dicyclohexylcarbodiimide, as described in Matteucci & Caruthers, J. Am. Chem. Soc., 1981, 103, 3185-3191.

The present invention will be better understood with the help of the following examples, which refer to the appended FIG. 1 in which the HPLC trace of an oligonucleotide of the invention exhibiting a ferrocene of the invention in the 3'-position is represented, and which are given purely by way of illustration and without implied limitation.

EXAMPLE 1

Synthesis of 1-[3-O-dimethoxytritylpropyl]-1'-[3'—O—(2-cyanoethyl-N,N-diisopropylphosphoramidityl)propyl]ferrocene 6

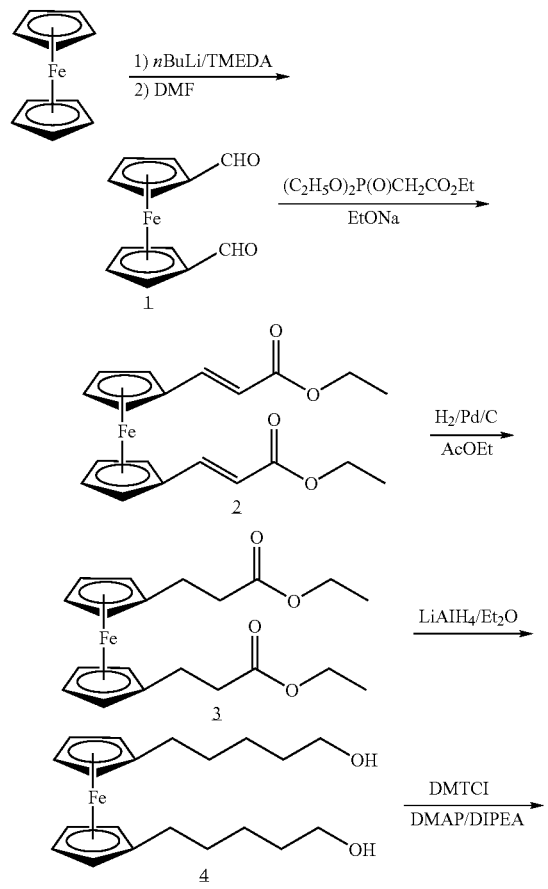

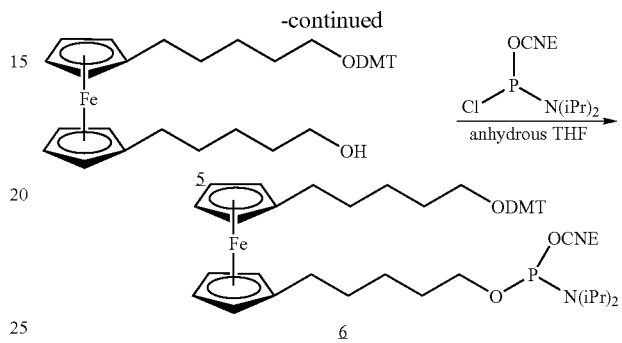

1.1 Synthesis of 1,1'-bisformylferrocene 1

1 g (5.37 mmol) of ferrocene, dissolved in 12 ml of anhydrous ethyl ether, was treated with 7.2 ml (11.56 mmol) of n-BuLi (1.6M solution in hexane) and by addition of 1.74 ml (11.56 mmol) of N,N,N',N'-tetramethylethylenediamine. The reaction was left under argon and with stirring at ambient temperature for 20 hours. 1.33 ml (17.20 mmol) of DMF were added at −78° C. After stirring at −78° C. for 2 hours, the reaction mixture was hydrolyzed (15 ml of water). The aqueous phase was extracted with dichloromethane (3×15 ml). The resulting organic phase was dried over MgSO$_4$ and was then concentrated. The residue was purified on silica gel with a pentane/ethyl acetate (50:50) mixture.

0.62 g (2.56 mmol, 48%) of compound 1 was obtained in the form of a brown paste.

$^1$H NMR (CDCl$_3$): 4.62 (d, J=9 Hz, 4H, H$_2$H$_3$—H$_2$H$_{3'}$), 4.83 (d, J=8.7 Hz, 4H, H$_1$H$_4$—H$_1$H$_{4'}$), 9.89 (m, 2H, 2CHO). $^{13}$C NMR (CDCl$_3$): 70.9 (C$_2$H$_5$), 74.20 (C$_3$C$_4$), 80.4 (C$_1$), 192.9 (C$_6$). MS: 185 (60), 243 (M$^{\cdot+}$, 95).

1.2 Synthesis of 1,1'-bis[(2-ethyloxycarbonyl)ethenyl]-ferrocene 2

0.094 g (4.08 mmol) of sodium and 25 ml of absolute ethanol were introduced into a 50 ml three-necked round-bottomed flask equipped with a reflux condenser and under argon. After the sodium had been completely consumed, the solution was cooled to 0° C. and then 0.809 ml (4.08 mmol) of ethyl diethylphosphonoacetate and 0.470 g (1.94 mmol) of ferrocene-1,1'-carboxaldehyde 1, dissolved beforehand in 10 ml of absolute ethanol, were added.

After returning to ambient temperature and evaporating, the residue was purified on silica gel with a cyclohexane/ethyl acetate (95:5) mixture.

0.560 g (1.46 mmol, 75%) of compound 2 was obtained in the form of red crystals.

$^1$H NMR (CDCl$_3$): 1.26 (t, J=7.15 and J=7.12 Hz, 6H, H$_9$H$_{10}$H$_{11}$—H$_9$H$_{10'}$H$_{11'}$), 4.15 (q, J=7.14 and J=7.11 Hz, 4H, H$_7$H$_8$—H$_7$H$_{8'}$), 4.31 (m, 4H, H$_2$H$_3$—H$_2$H$_{3'}$), 4.38 (m, 4H, H$_1$H$_4$—H$_1$H$_{4'}$), 5.91 (d, J=15.80 Hz, 2H, H$_6$—H$_{6'}$), 7.33 (d, J=15.79 Hz, 2H, H$_5$—H$_{5'}$). $^{13}$C NMR (CDCl$_3$): 14.2 (C$_{10}$), 60.1 (C$_9$), 69.7 (C$_2$H$_5$), 72.2 (C$_3$C$_4$), 79.9 (C$_1$), 116.2 (C$_7$), 143.7 (C$_6$), 166.9 (C$_8$).

MS: 382 (M$^{\cdot+}$, 85).

1.3 Synthesis of 1,1'-bis[(2-ethyloxycarbonyl)ethyl]-ferrocene 3

0.400 g (1.05 mmol) of compound 2, 0.100 g (0.94 mmol) of palladium-on-charcoal (10% Pd/C) and 40 ml of ethyl acetate were introduced into a 100 ml round-bottomed flask. The solution was carefully degassed by bubbling with a stream of argon (approximately 30 minutes). Hydrogen present in a balloon was bubbled in until the solution was saturated. A balloon of hydrogen was positioned above the assembly. The reaction mixture was then vigorously stirred for 48 to 72 hours.

After filtering and concentrating, 0.400 g (1.03 mmol, 99%) of compound 3 was obtained in the form of a yellow oil.

$^1$H NMR (CDCl$_3$): 1.19 (t, J=7.15 and J=7.12 Hz, 6H, $H_{11}H_{12}H_{13}$—$H_{11'}H_{12'}H_{13'}$), 2.43 (m, 4H, $H_7H_8$—$H_{7'}H_{8'}$), 2.57 (m, 4H, $H_5H_6$—$H_5H_{6'}$), 3.64 (S, 8H, $H_1H_2H_3H_4$—$H_{1'}H_{2'}H_{3'}H_{4'}$), 4.06 (q, J=7.13 and J=7.15 Hz, 4H, $H_9H_{10}$—$H_9H_{10'}$).

1.4 Synthesis of 1,1'-bis(3-hydroxypropyl)ferrocene 4

0.140 g (3.70 mmol) of LiAlH$_4$ was introduced, with stirring and under argon, into a three-necked round-bottomed flask equipped with a reflux condenser. 7 ml of anhydrous ethyl ether were added using a syringe. 1.43 g (3.70 mmol) of ester 3, dissolved in 9.5 ml of anhydrous ethyl ether, were added dropwise so as to maintain a constant reflux. The mixture assumed a viscous appearance, necessitating the addition of 15 ml of thoroughly anhydrous THF in order to facilitate the dissolution of the compounds. The reaction was monitored by TLC (elution: cyclohexane/ethyl acetate (80:20)). After stirring for 40 minutes, the excess lithium compound was decomposed by slow addition of water (15 ml) while continuing to stir. The formation of a white lithium hydroxide precipitate was observed.

After filtration, the aqueous phase was extracted with ethyl ether (2×25 ml). The organic phases were combined, dried over MgSO$_4$ and then concentrated.

0.810 g (2.68 mmol, 72%) of compound 4 was collected in the form of a yellow oil.

$^1$H NMR (CDCl$_3$): 1.54 (m, 4H, $H_7H_8$—$H_{7'}H_{8'}$), 2.12 (t, J=7.81 and J=7.08 Hz, 4H, $H_5H_6$—$H_5H_{6'}$), 3.43 (t, J=6.12 Hz, $H_9H_{10}$—$H_9H_{10'}$), 3.89 (m, 8H, $H_1H_2H_3H_4$—$H_{1'}H_{2'}H_{3'}H_{4'}$). $^{13}$C NMR (CDCl$_3$): 25.7 ($C_6$), 34.1 ($C_7$), 62.3 ($C_8$), 69.0 ($C_2H_5$), 64.4 ($C_3C_4$), 70.3 ($C_1C_2C_3C_4C_{5'}$), 89.1 ($C_1$). MS: 161 (21), 179 (40), 302 (M$^{\cdot+}$, 100).

1.5 Synthesis of 1-[3-O-dimethoxytritylpropyl]-1'-[3'-hydroxypropyl]ferrocene 5

200 mg (0.662 mmol) of 1,1'-dihydroxypropylferrocene 4 and 16 mg (0.132 mol) of DMAP were successively introduced into a 25 ml round-bottomed flask. After 2 successive coevaporations with 5 ml of anhydrous pyridine, the oil obtained was taken up in 5 ml of anhydrous pyridine. 247 mg (0.728 mmol) of 4,4'-dimethoxytrityl chloride and 115 µl (0.662 mmol) of N,N-diisopropylethylamine were added. The reaction mixture was left stirring at ambient temperature under a nitrogen stream. The progress of the reaction was monitored by TLC (elution: dichloromethane/methanol/TEA 89/10/1). After elution, the plates were systematically visualized in an ethanol/sulfuric acid mixture. After stirring at ambient temperature for 4 hours, 2 ml of methanol were added to the reaction mixture in order to neutralize the unreacted 4,4'-dimethoxytrityl chloride. After concentrating by half, the residue was taken up in dichloromethane (25 ml) and the solution was washed with a saturated aqueous NaHCO$_3$ solution and then with water (5×25 ml). After drying over MgSO$_4$ and concentrating, the crude product was coevaporated with 2×10 ml of toluene and was then left under vacuum overnight. The mixture was purified on silica gel (neutralized beforehand with TEA) with dichloromethane/methanol mixtures of increasing polarity.

304 mg (76%) of the monotritylated compound 5 were isolated. The latter exists in the form of an orange-colored oil.

$^1$H NMR (d$_6$-acetone): 1.64-1.72 (m, 2H, $H_7H_{8'}$), 1.75-1.86 (m, 2H, $H_7H_8$), 2.38-2.53 (m, 4H, $H_5H_6$—$H_5H_{6'}$), 3.08-3.14 (t, 2H, $H_9H_{10}$), 3.52-3.58 (t, 2H, $H_9H_{10}$), 3.78 and 3.79 (2s, 6H, —OCH$_3$), 3.95-3.98 (m, 8H, $H_1H_2H_3H_4$—$H_{1'}H_{2'}H_{3'}H_{4'}$), 6.82-7.68 (m, 13H, Ar).

1.6 Synthesis of 1-[3-O-dimethoxytritylpropyl]-1'-[3'—O—(2-cyanoethyl-N,N-diisopropylphosphoramidityl)propyl] ferrocene 6

255 mg (0.42 mmol) of the ODMT compound 5 and 7 mg (0.05 mmol) of DMAP were successively introduced into a 25 ml round-bottomed flask. After successive coevaporations with 2×2 ml of anhydrous pyridine and 2×2 ml of anhydrous THF, the residue was taken up in 3 ml of anhydrous THF. The reaction mixture was placed under a nitrogen stream and then 147 µl (0.84 mmol) of N,N-diisopropylethylamine were added all at once. 104 µl (0.46 mmol) of 2-cyanoethyl-diisopropylchlorophosphoramidite were then slowly added using a glass syringe (the addition lasts approximately 10 minutes). After half the addition, the formation of a precipitate was observed. After stirring at ambient temperature for 3 h 30, the reaction was monitored by TLC (elution: pentane/ethyl acetate 70/30). As the phosphoramidite formed is very reactive, it is not subjected to the treatment conventionally used. The crude product was concentrated by half. The silica column (fairly short) was set up with a pentane/TEA (0.5%) mixture, to neutralize the silica, and was then rinsed with pure pentane. After rapid deposition of the crude product, the product was eluted with a pentane/ethyl acetate (85/15) mixture while forcing with argon to accelerate the migration, in order to limit as far as possible contact of the product with the silica. After concentrating, 190 mg (56%) of an oil were obtained. The product was placed under vacuum for 12 hours and was then stored at –20° C.

Before use of this product in the synthesis of modified ODNs, it is preferable to confirm the possible presence of decomposition products by phosphorus NMR and to carry out a rapid purification of the product, if this proves to be necessary.

$^{31}$P NMR (CD$_3$CN): 148.25 (P).

EXAMPLE 2

Synthesis of a 22 mer Oligonucleotide 3'Fc-C7—NH$_2$ 7

The sequence of the ODN 7 is:

3'NH$_2$—C7—Fc-TGG AAT ACT CAG GTT CCT TAT G 5' (SEQ ID NO:1)

17 mg of support ((2-dimethoxytrityloxymethyl-6-fluorenylmethoxycarbonylamino-hexane-1-succinoyl)-long chain alkylamino-CPG 1000) functionalized to 59 µmol/g (Glen Research, Sterling, US) were introduced into a synthesis column (Applied Biosystems, Courtaboeuf, France). 100 mg of 6 (0.124 mmol) were dissolved in 1.24 ml of anhydrous acetonitrile (AB, France). The solution of 6 was used in the 5 position of an AB 394 synthesizer, according to the same protocol as for commercial phosphoramidites (A, C, G, T). The synthesis of the oligonucleotide 7 was carried out with the standard 1 µm program, the stage of which for the coupling of phosphoramidites was modified as follows: two withdrawals of 3.5 s of the phosphoramidite solution (instead of one withdrawal, as in the standard program), which are separated by a break of 15 s and which are followed by a break of 25 s. The overall coupling yield per cycle was 97.5%. After treatment of the CPG with 30% aqueous ammonia (55° C. for 16 h), the supernatant was concentrated on a Speed Vac. The product was taken up in 1 ml of $H_2O$ and 7 was purified on a preparative column (Merck LiChrospher RP18E, 12μ, 100 Å, 300×7.5).

The fractions were concentrated on a rotavapor and were then coevaporated 4 times with $H_2O$ before lyophilization in an Eppendorf tube. 15 OD (units of absorbance at 260 nm) of pure product were obtained.

The purity of the product was confirmed by HPLC analysis carried out on a Waters Deltapak $C_{18}$ 5μ 300 Å (3.9×150 mm) column. The chromatogram obtained at 260 nm is given in FIG. 1.

Mass spectrometry (MALDI-TOF), Voyager DE (Perseptive Biosystem):

theoretical mass m/z: 7352.9, observed mass m/z: 7338.3.

EXAMPLE 3

Preparation of a Support for the Synthesis of Oligonucleotides 3.1 Synthesis of the triethylammonium salt of 1-[3-O-(p,p'-dimethoxytrityl)propyl]-1'-[3'-O-(succinate)-propyl]ferrocene 8

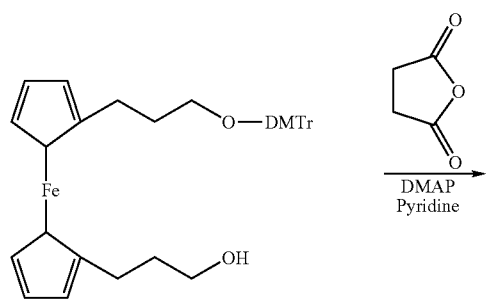

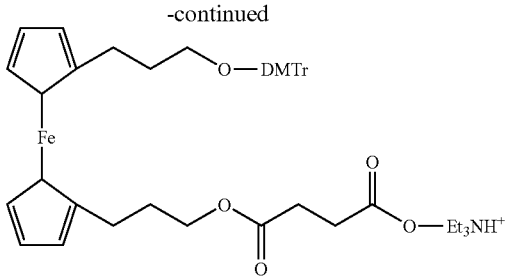

149 mg (247 μmol, 1 eq.) of 1-[3-O-(p,p'-dimethoxytrityl)propyl]-1'-[3'-hydroxypropyl]ferrocene, 5.67 mg (667 μmol, 2.7 eq.) of succinic anhydride and 7 mg (25 μmol, 0.1 eq.) of 4-N,N-dimethylaminopyridine (DMAP) were stirred with 180 ml (1.3 mmol, 5.3 eq.) of triethylamine in 2 ml of anhydrous dichloromethane under an inert atmosphere. After 3 h, the reaction mixture was partitioned between aqueous sodium bicarbonate (3×10 ml) and dichloromethane (40 ml). The organic phases were dried over sodium sulfate, were filtered, were evaporated and were purified on a column of silica gel (MeOH gradient in $CH_2Cl_2$) to give 160 mg (198 μmol, 80%) of desired product.

Rf (2% MeOH/$CH_2Cl_2$)=0.8

$^1$H NMR: δ ppm (CDCl$_3$): =7.34 (m, 9H, DMTr), 6.82 (m, 4H, DMTr), 4.12 (t, 2H, J=6.36 Hz, —CH$_2$OCOCH$_2$—), 3.96 (m, 8H, ferrocene), 3.79 (s, 6H, 2×OCH$_3$), 3.08 (m, 8H, —CH$_2$—O-DMTr), 2.64 (m, 4H, O—CO—CH$_2$—CH$_2$—COO$^-$), 2.42 (m, 4H, 2×CH$_2$-ferrocene), 1.82 (m, 4H, 2×CH$_2$CH$_2$—CH$_2$—).

3.2 Attachment to a Support of LCAA-CPG (Long Chain Alkylamine Controlled Pore Glass) Type

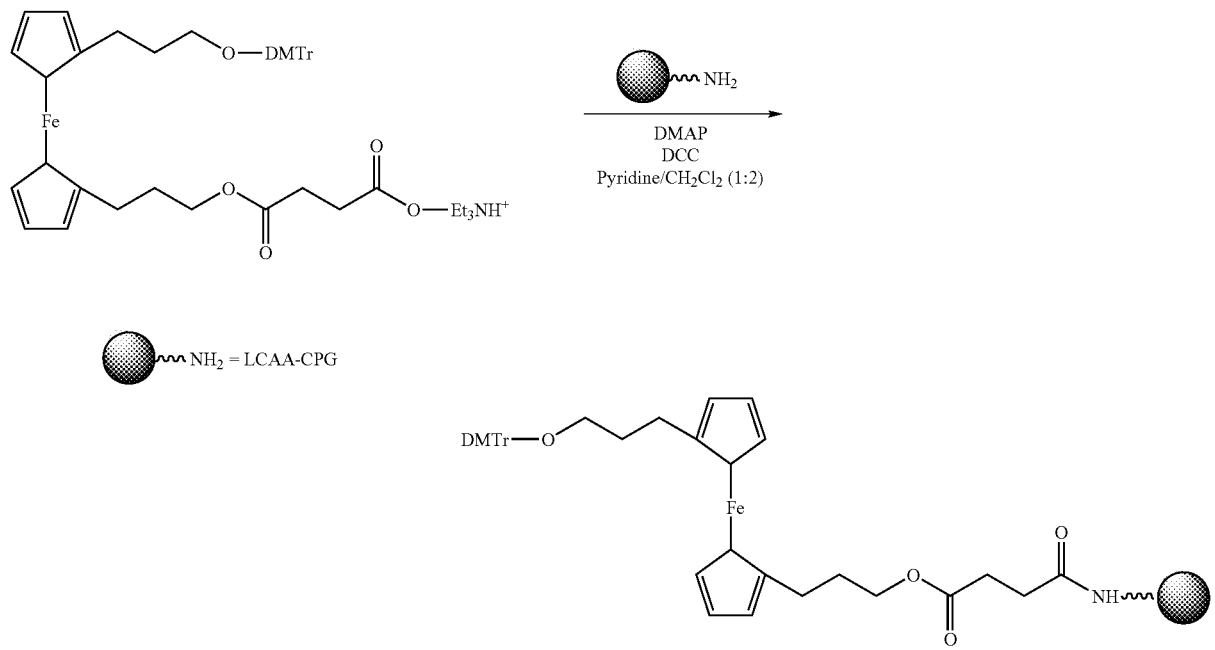

40.3 mg (50 µmol) of the triethylammonium salt of 1-[(p,p'-dimethoxytrityl)propanol]-1'-(propanol succinate) ferrocene obtained above, 500 mg of the LCAA-CPG (500 Å) support, 600 mg (3 mmol) of dicyclohexylcarbodiimide (DCC), 40 mg (0.32 mmol) of dimethylaminopyridine (DMAP) and 210 µl (1.5 mmol) of triethylamine were stirred mechanically in 3 ml of a pyridine/dichloromethane (½) mixture for 48 h. The silica beads were subsequently filtered off and were washed successively with pyridine, dichloromethane, methanol, dichloromethane and ether (50 ml of each).

The residual $NH_2$ functional groups were subsequently masked by reacting 1 ml of acetic anhydride with the CPG beads for 2 h in the presence of 1 ml of pyridine and 20 mg of DMAP. The beads were subsequently filtered off and were rinsed successively with dichloromethane, methanol, dichloromethane and ether (25 ml of each). They were dried under high vacuum until the sample reached a constant weight.

The functionalization of the support was evaluated by quantitatively determining the dimethoxytrityl cation released after having subjected an aliquot of support to an acid treatment. A functionalization of 0.1 µmol/mg was obtained.

What is claimed is:

1. A bifunctionalized metallocene of general formula (I):

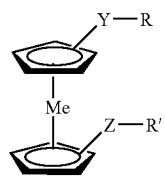

(I)

wherein:

Me represents a transition metal,

Y and Z, which are identical, are chosen from $-(CH_2)_n-O-$, $-(CH_2)-O-[(CH_2)_2-O]_p-$ and $-(CH_2)_q-CONH-(CH_2)_r-O-$, or else Y is $-(CH_2)_s-NH-$ and Z is $-(CH_2)_t-COO-$, n is an integer between 3 and 6, p is an integer between 1 and 4, q is an integer between 0 and 2, r is an integer between 0 and 2, s is an integer between 2 and 5, t is an integer between 3 and 6, R and R' represent hydrogen atoms or are protective groups used in the synthesis of oligonucleotides and peptides, wherein at least one of R or R' is a protective group used in the synthesis of oligonucleotides and peptides and that R and R' are as defined below:

(i) when Z and Y are chosen from $-(CH_2)_n-O-$, $-(CH_2)-O-[(CH_2)_2-O]_p-$ and $-(CH_2)_q-CONH-(CH_2)_r-O-$, then R and R' are protective groups used in the synthesis of oligonucleotides, and R is a group capable of leaving a free hydroxyl group after deprotection and R' is a phosphorus group capable of reacting with a free hydroxyl group, and (ii) when Y is $-(CH_2)_s-NH-$ and Z is $-(CH_2)_t-COO-$, then R is a protective group used in the synthesis of peptides and represents a protective group for amines, and R' represents a hydrogen atom.

2. The metallocene as claimed in claim 1, wherein Me is iron.

3. The metallocene as claimed in claim 1, wherein Y and Z are chosen from $-(CH_2)_n-O-$, $-(CH_2)-O-[(CH_2)_2-O]_p-$ and $-(CH_2)_q-CONH-(CH_2)_r-O-$.

4. The metallocene as claimed in claim 1, wherein Y and Z are each $-(CH_2)_n-O-$, n being equal to 3.

5. The metallocene as claimed in claim 1, wherein Y and Z are each $-(CH_2)-O-[(CH_2)_2-O]_p-$, p being equal to 2.

6. The metallocene as claimed in claim 1, wherein Y is $-(CH_2)_s-NH-$, Z is $-(CH_2)_t-COO-$.

7. The metallocene as claimed in claim 6, wherein s is equal to 3 and t is equal to 4.

8. A process for the preparation of a metallocene of formula (I) as claimed in claim 3, wherein it comprises the following stages:

a stage of protection of one of the hydroxyl groups of a compound of general formula (II):

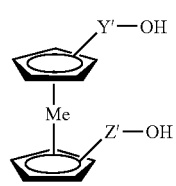

(II)

wherein:

Me represents a transition metal,

Y' and Z', which are identical, are chosen from —(CH$_2$)$_n$—, —(CH$_2$)—O—[(CH$_2$)$_2$—O]$_{p'}$—(CH$_2$)$_2$— and —(CH$_2$)$_q$—CONH—(CH$_2$)$_r$—, n is an integer between 3 and 6,
q is an integer between 0 and 2,
r is an integer between 0 and 2, and
p' is an integer between 0 and 3, by attachment of a group capable of leaving a free hydroxyl group after deprotection, and a stage of coupling, to the other hydroxyl group left free, a phosphorus group capable of reacting with a free hydroxyl group.

9. A process for the preparation of a metallocene of formula (I) as claimed in claim 6, wherein it comprises the following stages:

a stage of protection of the NH$_2$ group of a compound of general formula (III):

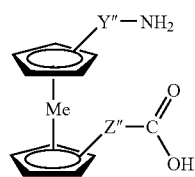

(III)

wherein:
Me represents a transition metal,
Y" is —(CH$_2$)$_s$— and Z" is —(CH$_2$)$_t$—,
s is an integer between 2 and 5,
t is an integer between 3 and 6, by attachment of a group capable of leaving a free amine functional group after deprotection.

10. A bis(hydroxy)metallocene of general formula (II):

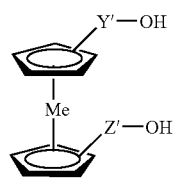

(II)

wherein:
Me is a transition metal,
Y' and Z', are each —(CH$_2$)—O—[(CH$_2$)$_2$—O]$_{p'}$—(CH$_2$)$_2$—, p' being equal to 0.

11. The bis(hydroxy)metallocene as claimed in claim 10, wherein Me is iron.

12. A process for labeling an oligonucleotide with a bifunctionalized metallocene of formula (I) as claimed in claim 3, wherein it comprises the substitution of one or more nucleotide synthons by one or more of said metallocenes of formula (I), in which R and R' are protective groups used in the synthesis of oligonucleotides, in the cycle for the synthesis of said oligonucleotide.

13. The process as claimed in claim 12, wherein the substitution is carried out in the 3'- or 5'-positions in replacement of the first or last nucleotides, respectively.

14. A process for labeling a peptide by a bifunctionalized metallocene of formula (I) as claimed in claim 6, wherein it comprises the substitution of one or more amino acid synthons by one or more of said metallocenes of formula (I), in which R represents a protective group for amines and R' represents a hydrogen atom, in the cycle for the synthesis of said peptide.

15. The process as claimed in claim 14, wherein the substitution is carried out at the C-terminal or N-terminal ends in replacement of the first or last amino acids, respectively.

16. The process as claimed in claim 12, wherein at least two consecutive substitutions are carried out.

17. A labeled oligonucleotide, wherein it is capable of being obtained by the labeling process as claimed in claim 12.

18. A labeled oligonucleotide, wherein at least one of the nucleosides constituting it is substituted by a bis(hydroxy) metallocene of general formula (II) as claimed in claim 10.

19. The labeled oligonucleotide as claimed in claim 17, wherein it comprises at least one of bis(hydroxy)metallocene of general formula (I) in the 3'- or 5'-position.

20. A labeled peptide, wherein it is capable of being obtained by the process as claimed in claim 14.

21. A labeled peptide, wherein at least one of the aminoacids constituting it is substituted by a bifunctionalized metallocene of formula (III) as defined in claim 9.

22. The peptide as claimed in claim 20, wherein it comprises at least one bifunctionalized metallocene of formula (III) at the C-terminal or N-terminal ends.

23. A support for the synthesis of oligonucleotides, wherein at least one metallocene of formula (I) as claimed in claim 1, is grafted to said support by covalent reaction of one of its functionalized ends.

24. The bifunctionalized metallocene of general formula (I) as claimed in claim 1, wherein Me is selected from the group consisting of Fe, Ru, and Os.

25. The bifunctionalized metallocene of general formula (I) as claimed in claim 1, wherein when Z and Y are chosen from —(CH$_2$)$_n$—O—, —(CH$_2$)—O—[(CH$_2$)$_2$—O]$_p$— and —(CH$_2$)$_q$—CONH—(CH$_2$)$_r$—O—, R is selected from the group consisting of a photolabile group, monomethoxytrityl, dimethoxytrityl, tert-butyldimethylsilyl, acetyl, and trifluoroacetyl.

26. The bifunctionalized metallocene of general formula (I) as claimed in claim 1, wherein when Z and Y are chosen from —(CH$_2$)$_n$—O—, —(CH2)—O—[(CH$_2$)$_2$—O]$_p$— and —(CH$_2$)$_q$—CONH—(CH$_2$)$_r$O—, R' is selected from the group consisting of phosphodiester, phosphoramidite, and H-phosphonate group.

27. The bifunctionalized metallocene of general formula (I) as claimed in claim 1, wherein when Y is —(CH$_2$)$_s$—NH— and Z is —(CH$_2$)$_t$—COO—, R is selected from the group consisting of 9-fluorenyloxycarbonyl, tert-butoxycarbonyl, and benzyloxycarbonyl.

* * * * *